US008820061B2

(12) United States Patent
Gmelin

(10) Patent No.: US 8,820,061 B2
(45) Date of Patent: Sep. 2, 2014

(54) METHOD FOR ACTUATING A HYDRAULICALLY MOVABLE WORKING ELEMENT OF A WORKING EQUIPMENT, AND A WORKING EQUIPMENT

(75) Inventor: Wolfgang Gmelin, Oestringen (DE)

(73) Assignee: Toni Kiesel, Ravensburg (DE)

( * ) Notice: Subject to any disclaimer, the term of this patent is extended or adjusted under 35 U.S.C. 154(b) by 499 days.

(21) Appl. No.: 13/138,828

(22) PCT Filed: Jun. 7, 2011

(86) PCT No.: PCT/EP2011/059374

§ 371 (c)(1),
(2), (4) Date: Oct. 5, 2011

(87) PCT Pub. No.: WO2011/154396

PCT Pub. Date: Dec. 15, 2011

(65) Prior Publication Data

US 2012/0312003 A1 Dec. 13, 2012

(30) Foreign Application Priority Data

Jun. 11, 2010 (DE) ......................... 10 2010 023 435

(51) Int. Cl.

| | |
|---|---|
| ***F16D 31/00*** | (2006.01) |
| ***F16D 33/00*** | (2006.01) |
| ***F16D 37/00*** | (2006.01) |
| ***F16D 31/02*** | (2006.01) |
| ***F15B 11/08*** | (2006.01) |
| ***F15B 11/00*** | (2006.01) |
| ***A01H 5/02*** | (2006.01) |

(52) U.S. Cl.
USPC ................... 60/327; 60/484; 91/436; 91/519; 91/471

(58) Field of Classification Search
CPC .................... F15B 11/024; F15B 2211/30525; B60K 17/105
USPC .............. 91/436, 471, 516, 534; 60/414, 427, 60/484
See application file for complete search history.

(56) References Cited

U.S. PATENT DOCUMENTS 3,228,306 A * 1/1966 Pedersen ......................... 91/436
3,481,251 A 12/1969 Shook (Continued)

FOREIGN PATENT DOCUMENTS

DE 1919759 A1 11/1970
DE 2 342 942 A1 3/1974

(Continued)

OTHER PUBLICATIONS

International Search Report dated Aug. 3, 2011, from corresponding PCT Appln. No. PCT/EP2011/059374.

(Continued)

*Primary Examiner* — Edward Look
*Assistant Examiner* — Daniel Collins
(74) *Attorney, Agent, or Firm* — Kriegsman & Kriegsman

(57) ABSTRACT

The invention relates to a method and to a working equipment for actuating a hydraulically movable working element (24), which is provided on a main body (14) of a working equipment (11), comprising at least one main cylinder (19) and at least one additional cylinder (28), which are supplied with pressure medium to generate a pivoting movement, wherein the pivoting movement in the rapid motion mode is actuated in a first working pressure range of the hydraulic control device (32), the pivoting movement in a working motion mode is actuated in a second working pressure range, which is higher than the first working pressure range, the pivoting movement in the heavy load motion mode is actuated in a third working pressure range, which is higher than the first and second working pressure ranges, and the pivoting movement of the working element (24) in the operating modes of rapid motion, working motion or heavy load motion is actuated in accordance with the prevailing working pressure.

20 Claims, 8 Drawing Sheets

(56) References Cited

U.S. PATENT DOCUMENTS

Figure 1B:
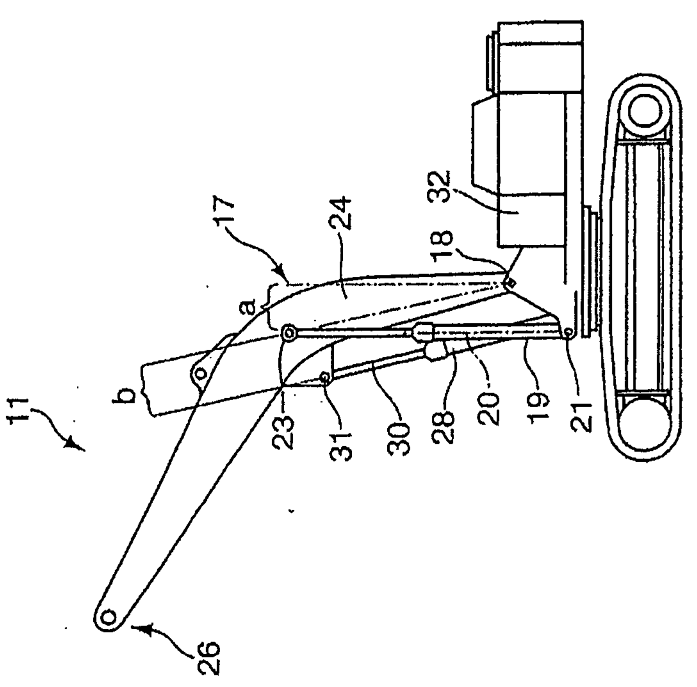

| | | | | | |
|---|---|---|---|---|---|
| 3,664,527 | A | | 5/1972 | Short | |
| 5,168,705 | A | * | 12/1992 | Hirata et al. | 60/452 |
| 5,467,829 | A | | 11/1995 | Barton et al. | |
| 5,878,569 | A | * | 3/1999 | Satzler | 60/418 |
| 6,161,467 | A | * | 12/2000 | A'Hearn et al. | 91/436 |
| 6,502,393 | B1 | * | 1/2003 | Stephenson et al. | 60/414 |
| 2002/0011013 | A1 | | 1/2002 | Sawada et al. | |
| 2007/0130808 | A1 | | 6/2007 | Peterson et al. | |

FOREIGN PATENT DOCUMENTS

| | | | |
|---|---|---|---|
| DE | 24 35 676 | A1 | 2/1975 |
| DE | 2434623 | A1 | 2/1975 |
| DE | 2435676 | A1 | 2/1975 |
| DE | 31 20 110 | A1 | 2/1982 |
| DE | 3120110 | A1 | 2/1982 |
| EP | 2 146 009 | A1 | 1/2010 |
| EP | 2146009 | A1 | 1/2010 |
| GB | 2076777 | A | 12/1981 |
| WO | 03064775 | A1 | 8/2003 |

OTHER PUBLICATIONS

International Preliminary Report on Patentability dated Dec. 14, 2012, from corresponding PCT Appln. No. PCT/EP2011/059374.

* cited by examiner

METHOD FOR ACTUATING A HYDRAULICALLY MOVABLE WORKING ELEMENT OF A WORKING EQUIPMENT, AND A WORKING EQUIPMENT

The invention relates to a method for actuating a hydraulically movable working element of a working equipment and to a working equipment of this type.

For example, working equipments comprising movable working elements are excavators or cranes having booms which receive an attachment, generally in a replaceable manner, on a boom serving as a working element. For example, an attachment of this type may be a clamshell bucket or an orange peel grab, a lifting hook, a pair of pincers, a scoop or the like. Furthermore, working equipments of this type may be scrap recycling devices, such as scrap cutters, in which the working element is designed as a pivotable jaw with a working edge for cutting or crushing materials. The field of application of such working equipments basically depends on the size of the working range and on loading capacities. It is often desired to be able to transfer high loads in particular in the immediate vicinity of the working equipment. For example, an exemplary application of this type is the lifting of pipelines. Once a trench has been dug, the pipe is to be laid therein. In order to fully utilise the working equipment, the attachment is changed so as to carry out these two activities one after the other.

DE 31 20 110 A1 discloses a hydraulic loading device comprising a boom, a pivoting arm and a loading bucket which are moved using hydraulic booms and arm cylinders. A first single-action lifting cylinder is arranged between a bearing arm and a revolving superstructure, and a second double-action lifting cylinder is arranged parallel thereto. A third lifting cylinder is positioned between the bearing arm and the pivoting arm, and a fourth lifting cylinder is positioned between the pivoting arm and a bucket. The individual working cylinders are actuated by a complex hydraulic control device, wherein a simple switching of the hydraulic control from a rapid motion mode during the working cycle of the bearing arm in order to take up an increased load is not provided.

Furthermore, a working equipment comprising hydraulic cylinders is known from DE 24 34 623 A1, as a result of which the bearing arm is moved up and down. The lifting cylinders are actuated in such a way that a uniform course of lifting power over the entire lifting movement is induced and therefore a switching between a rapid motion mode and a heavy load motion mode, i.e. a working cycle for lifting loads, is not provided.

Furthermore, a working equipment is known from DE 24 35 676, in which a working cylinder for the up and down movement of a bearing arm is provided and a second working cylinder is merely used as an energy store without assisting, in terms of force, the first lifting cylinder for the pivoting movement.

Furthermore, DE 2 342 942 discloses a working equipment comprising a hydraulic control of a bearing arm. The bearing arm is moved up and down via a first lifting cylinder arranged between the revolving superstructure and said bearing arm. A second lifting cylinder arranged between the revolving superstructure and the bearing arm supports a third lifting cylinder, which is provided between the bearing arm and the bucket, so as to achieve a synchronised movement of the bucket to maintain a set bucket angle.

Furthermore, a working equipment is known from EP 2 146 009 A, in which a first main cylinder pair engages with a bearing arm and an additional cylinder is attached at a different point of engagement. The main cylinder pair and the lifting cylinder arranged therebetween are each interconnected via separate hydraulic circuits. The individual lifting cylinder between the main cylinder pair serves merely as an energy store, that is to say the up and down movement of the bearing arm is actuated exclusively by the main cylinder pair. The pivoting movement of the bearing arm therefore cannot be actuated in a rapid motion mode or in a heavy load motion mode in an application-specific manner.

The object of the invention is to propose a method for actuating a hydraulically movable working element comprising at least one main cylinder and at least one additional cylinder in a working equipment, and a working equipment for handling loads comprising at least one main cylinder and at least one additional cylinder, in such a way that it is possible to actuate a working element in a versatile manner in different working ranges.

This object is achieved in accordance with the invention by a method for actuating a boom, which is moveable up and down hydraulically, of a working equipment having the features of claim 1. Further advantageous embodiments of the method are disclosed in the further claims dependent on claim 1.

In the method according to the invention at least one main cylinder and at least one additional cylinder are provided to actuate the working element and engage between the main body and the working element, in particular between the revolving superstructure and the bearing arm, so as to produce a pivoting movement of the working element, wherein the main and additional cylinders each comprise a connection on the piston chamber side and a connection on the piston rod side and are supplied via pressure lines of a hydraulic control unit and, in order to pivot the working element, are supplied with a pressure medium which is pressurised from a tank by means of pumps, and in each case the connections on the piston chamber side or the connections on the piston rod side of the at least one main cylinder and of the at least one additional cylinder are operated as pressurised connections. The pivoting movement in the rapid motion mode is actuated in a first working pressure range, the pivoting movement in a working motion mode is actuated in a second working pressure range, which is higher than the first working pressure range, and the pivoting movement in the heavy load motion mode is actuated in a third working range, which is higher than the first and second working pressure ranges, wherein the pivoting movement in the operating modes of rapid motion, working motion or heavy load motion is actuated in accordance with the respective working pressure or is transferred to the working mode. As a result of this method, it is possible to obtain ideal working pressures for generating the pivoting movement for any loading situation of the working element in a working range. Furthermore, an optimal adaptation to differently acting forces in different positions within a working range can be considered and a pivoting movement can be effected. An almost continuous switching between the individual working pressure regions preferably occurs so that a continuous pivoting movement or working movement of the working element can be implemented.

In accordance with a preferred embodiment of the method the pressure medium is fed from a tank of the working equipment to each of the pressurised connections of the at least one main and additional cylinders in the first working pressure range, in which the pivoting movement is actuated in the rapid motion mode, and the unpressurised connections of the respective main and additional cylinders are connected to the corresponding pressurised connections of the respective main and additional cylinders by a respective bypass circuit so that in each case the pressure medium discharged from the main and additional cylinders is carried off via the unpressurised connections and is fed into the pressurised connection of the same main and primary cylinders. This circuit arrangement in the first working pressure range affords the advantage that a shortened return of the pressure medium carried off from the main and additional cylinders is made possible. The pressurised chamber of the main and additional cylinders can be filled more quickly. Furthermore, a reduction in the frictional loss in the line-mounted valve is achieved. This means that a higher working speed can be implemented in the rapid motion mode.

In accordance with a further preferred embodiment of the method, in the second working pressure range, which is higher than the first working pressure range and in which the pivoting movement is actuated in the working motion mode, the unpressurised connection of the main cylinder is connected to a tank for feeding the discharged medium and the bypass circuit is maintained between the unpressurised and pressurised connections of the additional cylinder. As a result of this embodiment, it is possible for the working speed of the rapid motion mode to be maintained in such a way that a decreasing pressure difference in the main cylinder between the pressurised and unpressurised connections can be counteracted. In the case of this working motion mode, the at least one additional cylinder is carried over or entrained, preferably without loading, since the bypass circuit thereof is maintained and pressure medium can be additionally fed to the bypass circuit via a hydraulic line from the tank in order to sufficiently fill the pressure chamber of the additional cylinder.

In a further embodiment of the method, in the third working pressure range, which is higher than the first and second working pressure ranges and in which the pivoting movement is actuated in the heavy load motion mode, the unpressurised connections of the at least one main cylinder and additional cylinder are connected to the tank. The at least one main and additional cylinders are thus pressurised to the maximum by an increased to maximum working pressure of the hydraulic control unit.

In accordance with a preferred embodiment of the method, the working pressure is monitored during the pivoting movement of the working element by at least one control element and a first working pressure value is preset between the first and second working pressures, a second working pressure value is preset between the second and third working pressure ranges, and if the respective working pressure value is exceeded or is not met, the corresponding operating mode of the working pressure range is actuated. It is thus made possible, for example during a pivoting movement of the working element, for an overload occurring for the rapid motion mode to not lead to a stoppage of the pivoting movement, but to a continuation of the desired pivoting movement and a switching within the hydraulic control such that the main cylinders still control the pivoting movement. Owing to this control, it is thus possible for a pivoting movement to be started, for example in the rapid motion mode, in the working motion mode or in the heavy motion mode, and a corresponding switching into the respective other operating mode is enabled in accordance with the subsequent working pressures. Owing to such a selective control of the operating mode, an optimal lifting power can be generated during the pivoting movement of the working element.

In accordance with a further preferred embodiment of the method the at least one additional cylinder is operated as a damping cylinder during the lowering movement of the boom and counteracts the at least one main cylinder, which carries out the lowering movement. An additional controlled lowering of the boom from a close range into a working range distanced further therefrom can thus be enabled in a controlled manner. In addition, a damping with maximum loading of the first main cylinder or of the main cylinder pair can be achieved.

The object is further achieved in accordance with the invention by a working equipment having a boom, which is moveable hydraulically up and down, according to the features of claim 7. Advantageous embodiments of the working equipment are disclosed in the further claims.

In the embodiment according to the invention of a working equipment comprising a hydraulically movable working element in which at least one main cylinder and at least one additional cylinder are arranged pivotably on a main body and engage opposite with a working element which is also arranged pivotably on the main body and, depending on the respective working pressure, is actuatable by a first, second and third circuit arrangement by at least one control element depending on the prevailing working pressure, a load-adapted actuation of the working element is enabled in a working range for an up and down or to and fro movement.

In a first preferred circuit arrangement for actuating the pivoting movement in the rapid motion mode, the unpressurised connection of the at least one main cylinder and of the at least one additional cylinder for returning the discharged medium during the working motion is connectable to the respective pressurised connection of the same main and additional cylinders and therefore a first bypass circuit is formed for the main cylinder(s) and second bypass circuit is formed for the additional cylinder(s). The bypass circuit of the at least one main cylinder is formed separately from the bypass circuit of the at least one additional cylinder. As a result of the bypass circuits it is made possible for the discharged pressure medium to be fed back to the respective hydraulic cylinder during the working motion thereof in a first working phase of the rapid motion mode so as to fill the respective pressure chamber more quickly, such that a rapid motion mode with a high working speed is actuatable.

Owing to a feed line, additional pressure medium is preferably fed to the respective bypass circuits in the rapid motion mode in at least a first working phase. As a result, the pressure chambers of the main and additional cylinders are supplied and filled by fed pressure medium from the tank and also by pressure medium carried off from the specific hydraulic cylinder in question.

Furthermore, a second circuit arrangement of the hydraulic control device is preferably provided, in which a working motion mode is actuatable. In this case the unpressurised connection and the pressurised connection of the at least one additional cylinder are connected in a bypass so that a bypass circuit for the additional cylinder is formed. With regard to the at least one main cylinder, the respective pressurised connection is supplied with pressure medium from the tank and the unpressurised connection feeds the discharged pressure medium into the tank. Owing to this second circuit arrangement, an operating mode is enabled in which the at least one main cylinder is exposed to a working pressure and the at least one additional cylinder is entrained almost without force. In addition, in particular during an extending movement, an undersupply of the filling volume in the pressure chamber of the additional cylinder is compensated for by the feed line leading to the bypass circuit, which feed line supplies the at least one main cylinder with pressure medium.

Furthermore, a heavy load motion mode is preferably actuatable by a third circuit arrangement. With this circuit arrangement both the connections on the pressure chamber side of the at least one main cylinder and of the at least one additional cylinder and the respective unpressurised connections of the least one main cylinder and additional cylinder are connected to the tank.

In a preferred embodiment of the invention, during a lifting movement of the working element in the close range of the working range, the at least one additional cylinder has a larger lever arm relative to the bearing arm than the main cylinder or the main cylinder pair. An increased load is thus made possible, even in the close range, that is to say a greater load can be lifted and handled or applied. For example, conventional working equipments can also be used and converted for lifting heavy loads in the close range. In particular, this is based on the fact that different attachments can be arranged on the boom, generally via a changing system, for example so that a working equipment can receive a gripper or lifting hook or else a scrap cutter or the like, and therefore has a wider field of application and is utilised to a greater extent.

In accordance with a further preferred embodiment of the invention the main cylinder or the main cylinder pair comprises a point of engagement on the working element which is formed differently from the point of engagement of the at least one additional cylinder, wherein in particular a different distance from the bearing axis of the working element on the main body is provided. Different lever arms can thus be formed in a simple manner, wherein at the same time a good adaptation to the constructional features of any boom can be considered. In particular the distance between the at least one additional cylinder and the bearing axis of the working element on the main body is greater than the distance between the point of engagement of the first lifting cylinder or main cylinder pair and the bearing axis of the working element on the main body.

In a further preferred embodiment of the invention, in order to take up an increased load in the close range of the working range, the at least one additional cylinder engages at an angle of engagement which differs from that of the first lifting cylinder or main cylinder pair. As a result, in particular with a lifting movement in the close range, the at least one additional cylinder may comprise a larger lever arm than the main cylinder or the main cylinder pair so as to apply the additional compressive force to increase the load.

In accordance with an alternative embodiment of the invention a longitudinal axis of the at least one additional cylinder is arranged parallel to the longitudinal axis of the first lifting cylinder or main cylinder pair. Owing to the different points of engagement, an enlarged lever arm may thus again also be formed.

In a preferred embodiment of the working equipment the working element is formed as a bearing arm and the bearing arm of a boom is formed in a number of parts from a bearing arm stump and at least one bearing arm portion and comprises a changing device for receiving the bearing arm portion in a replaceable manner, and the at least one additional cylinder engages with the bearing arm stump of the boom. This arrangement makes it possible to simplify the interface at the changing device, since the hydraulic control comprises a valve which connects at least one additional cylinder as required.

In an alternative embodiment of the working equipment the bearing arm of the boom is formed in a number of parts and comprises a changing device on which a bearing arm portion can be arranged, and the at least one additional cylinder engages with the bearing arm portion. This arrangement affords the advantage that conventional working equipments, in which most fields of application are covered by the first cylinder or the main cylinder pair for an up and down movement of the boom, can be formed in a cost effective manner and the at least one additional cylinder is connected and incorporated in the hydraulic control, merely as required when lifting and lowering increased loads by means of a bearing arm portion of the at least one additional cylinder. A further control valve is preferably provided in order to control further hydraulic cylinders.

In accordance with a further preferred embodiment of the invention the at least one additional cylinder arranged on the bearing arm portion remains connected thereto when said bearing arm portion is changed. On the one hand this affords the advantage that a simple dismantling of the working equipment to form a single-cylinder or double-cylinder drive is enabled. On the other hand the lifting cylinder is preferably arranged on the bearing arm portion in such a way that a hydraulic line opens out directly into the piston chamber of the lifting cylinder and a valve is accordingly opened or closed in the changing device, whereby assembly is simplified. At the same time, this additional cylinder can serve as a support in a receiving region or positioning region for the bearing portion so as to position the changing device at a suitable engagement height.

In a further preferred embodiment of the invention, in the case of a multi-part boom in which the at least one additional cylinder is fixed to a bearing arm portion which can be replaced on the bearing arm stump, said boom is actuated by a further valve. For example, the bearing arm stump comprising a first lifting cylinder or a main cylinder pair can receive a bearing arm portion comprising a scoop arranged thereon, whereby the working equipment can be used as a conventional excavator. However, if this excavator is to be used as a loading crane or the like, owing to the multi-part boom an additional cylinder may be fixed to the bearing stump or bearing arm portion so that, in particular in the close range, increased loads can be lifted. In order to actuate the at least one additional cylinder, a further valve is provided which is connected to the hydraulic control as soon as the at least one additional cylinder is connected to the bearing arm stump via the bearing arm portion.

In a further preferred embodiment of the invention the at least one additional cylinder is arranged adjacent to a first lifting cylinder or between a lifting cylinder pair. For example, lifting cylinders engaging with the bearing arm can thus all be positioned on the same side or in the same region of the bearing arm.

In an alternative embodiment of the working equipment the at least one additional cylinder is designed as a stick cylinder between the main body formed from the revolving superstructure and the working element formed as a bearing arm. Such an arrangement is generally provided if a region between the main cylinder pair is too narrow to provide an additional cylinder therein. This is therefore arranged rearwards.

In accordance with a further preferred embodiment of the invention, in the case of a multi-part boom comprising at least two bearing arms mounted pivotably in relation to one another, at least one additional cylinder is arranged between the two bearing arms arranged pivotably in relation to one another, wherein the at least one additional cylinder comprises a lever arm different from the first lifting cylinder or main cylinder pair between the two bearing arms. These previously described embodiments can also be formed similarly in the case of the multi-part boom. Very wide and multi-part booms may thus also comprise a high load in the close range.

Figure 1A:
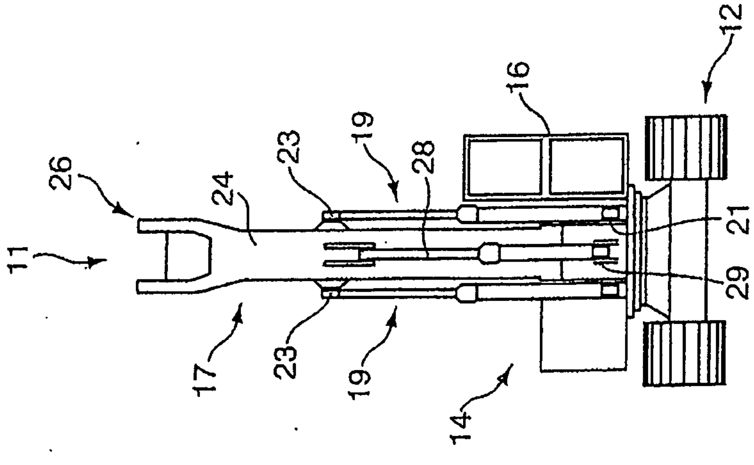
Figure 3:
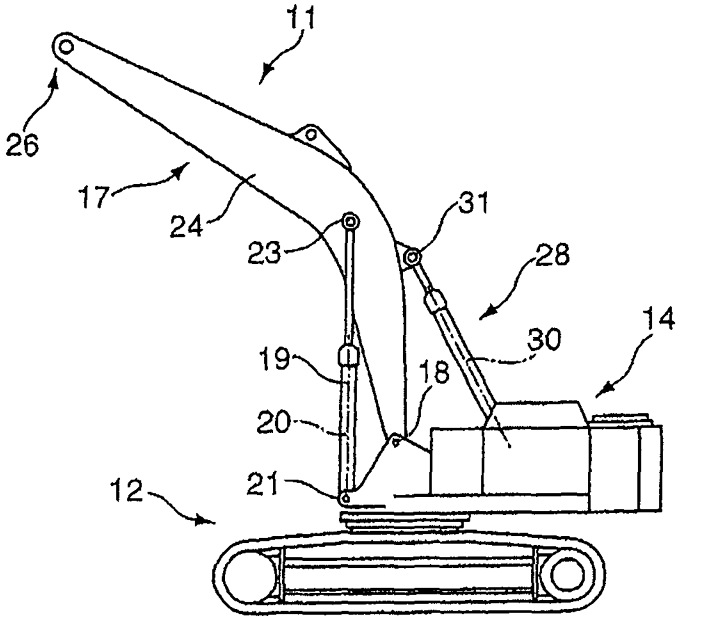

The invention and further advantageous embodiments and developments thereof will be described hereinafter in greater detail with reference to the examples illustrated in the drawings. The features to be deduced from the description and the drawings can be applied individually or together in any combination in accordance with the invention. In the drawings:

FIGS. 1*a* and *b* are schematic side views of a working equipment;

FIGS. 2*a* to *f* are schematic sectional views of a hydraulic control device of the working equipment in different circuit arrangements;

FIG. 3 is a schematic view of an alternative working equipment to FIGS. 1*a* and 1*b;*

Figure 4B:
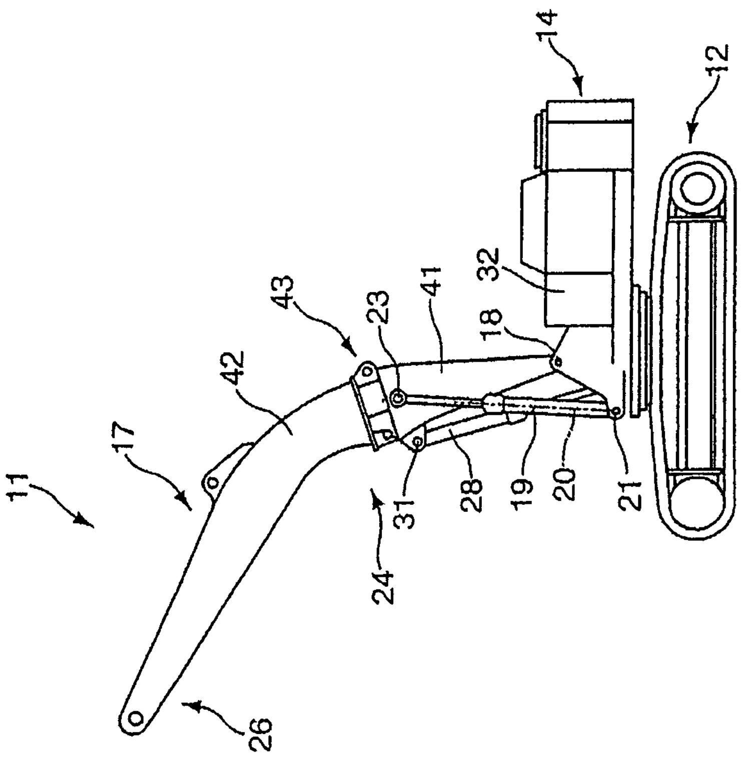
Figure 4A:
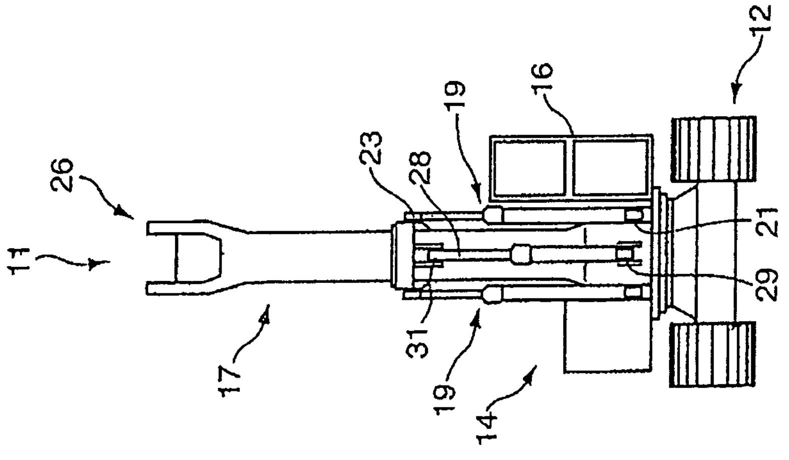

FIGS. 4*a* and *b* are schematic sectional views of a further alternative embodiment to FIGS. 1*a* and 1*b;*

Figure 5:
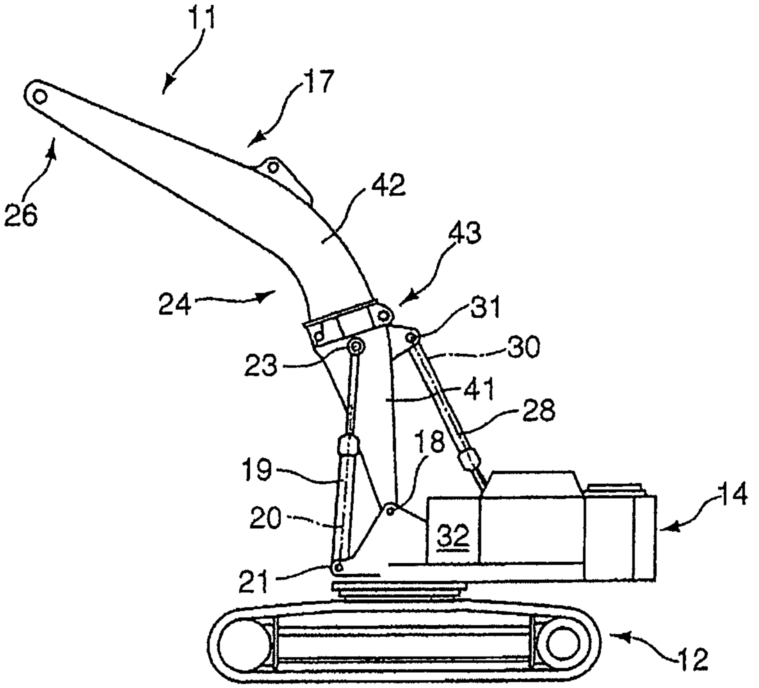

FIG. 5 is a schematic side view of an alternative embodiment to FIGS. 4*a* and *b;*

Figure 7:
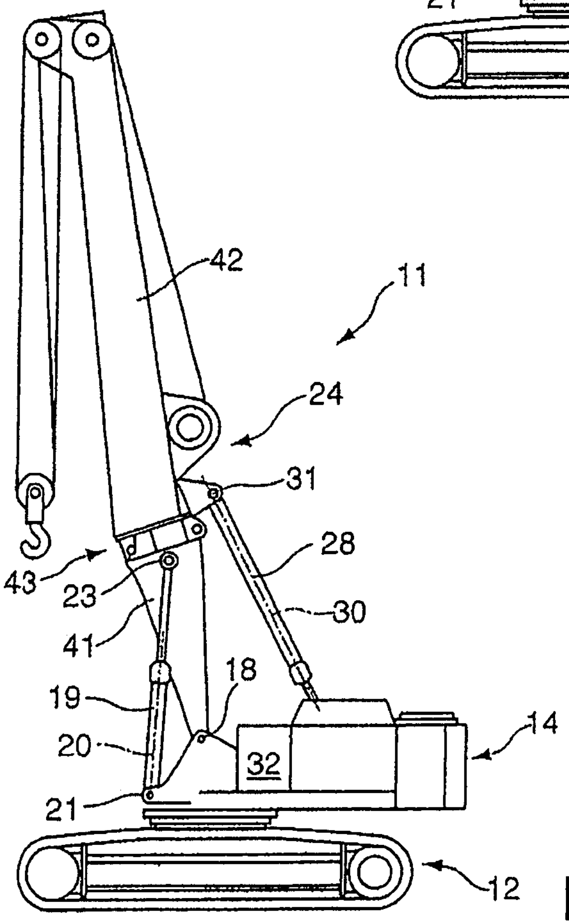
Figure 6A:
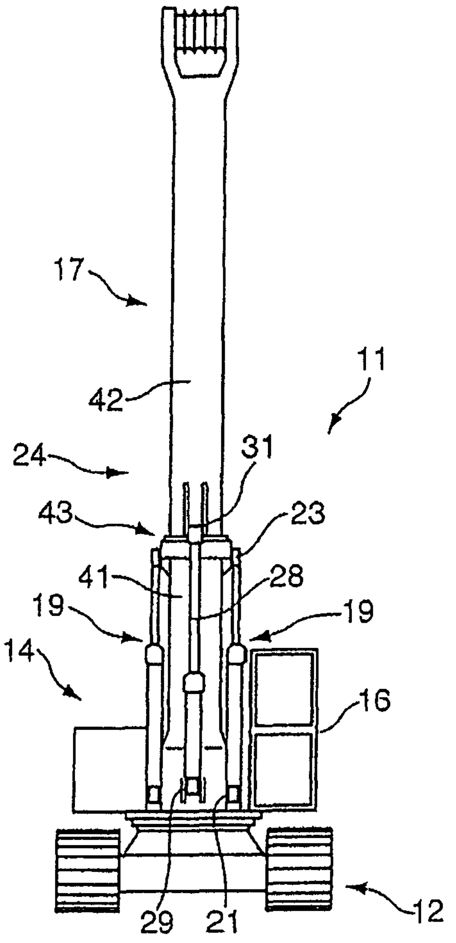
Figure 6B:
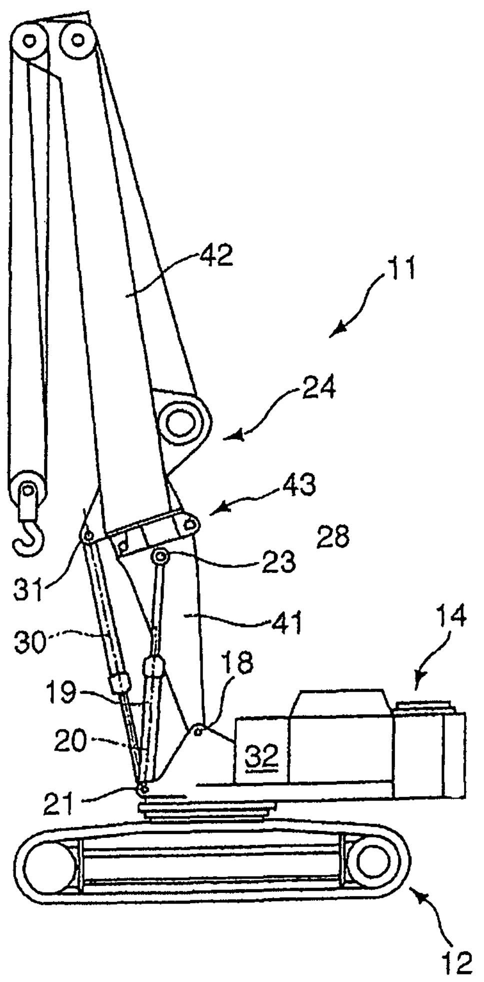

FIGS. 6*a* and *b* are schematic side views of a further alternative embodiment to FIGS. 4*a* and 4*b*; and FIG. 7 is a schematic side view of a further alternative embodiment to FIGS. 6*a* and 6*b.*

Schematic side views of a working equipment 11 according to the invention are shown in FIGS. 1*a* and *b*. Such a working equipment 11 may, for example, be an excavator, which is shown in FIGS. 1*a* and *b*. Alternatively, such working equipments 11 may also be "waste shears", which comprise one pivotable and one fixed jaw or two jaws pivotable in relation to one another. This working equipment 11 designed as an excavator comprises an undercarriage 12 which can be moved via a chain. Alternatively, running wheels or tyres may be provided. A main body 14 is provided rotatably on the undercarriage 12 and will be described hereinafter on the basis of the selected embodiment as a revolving superstructure 14 on which a driver's cabin 16 is arranged which is only shown in FIG. 1*a*. A boom 17 is arranged on the revolving superstructure 14 so as to be pivotable or movable up and down about a bearing axis 18. A main cylinder pair formed of two main cylinders 19 is provided for the lifting and lowering movement in the working range of the boom 17, which main cylinders are mounted pivotably on the revolving superstructure 14 via a bearing axis 21 and engage opposite at a point of engagement 23 with a working element 24. This will be referred to hereinafter with reference to the selected embodiment as a working element 24 of the boom 17. Alternatively, instead of two main cylinders 19 which engage with the boom 17 in the same bearing axis 21 and at the same points of engagement 23 to the left and right of the bearing arm 24, only one main cylinder 19 may be provided.

In this working equipment 11 the boom 17 consists of a single, for example rigid bearing arm 24, which preferably comprises a receptacle 26 in its front free end, to which different shaft designs can be attached. Alternatively, the boom 17 may also comprise a number of bearing arms 24 which are interconnected in an articulated manner.

In order to increase a bearing load in the close range of the working range of the working equipment 11, at least one additional cylinder 28 is provided which is supported on the revolving superstructure 14 via a bearing axis 29 and is fixed on the bearing arm 24 at a point of engagement 31. For example, this point of engagement 31 of the additional cylinder 28 differs from the point of engagement 23 of the first lifting cylinder or main cylinder pair 19 so that, in particular in a working position, the additional cylinder 28 has a larger lever arm than the main cylinder 19 or the main cylinder pair in the close range of the boom 17. This is apparent in the arrangement according to FIG. 1, since in an uppermost position of the boom 17 the main cylinder 19 is extended fully and protrudes vertically upwards and the lever arm a is thus smaller than the lever arm b of the at least one additional cylinder 28. In particular with a lifting movement in the close range, an additional force is introduced via the additional cylinder 18 to increase the load. In this embodiment the main or additional cylinder 19, 28 is oriented in such a way that the piston rods engage with the boom 17 at the points of engagement 23, 31.

Figure 2A:
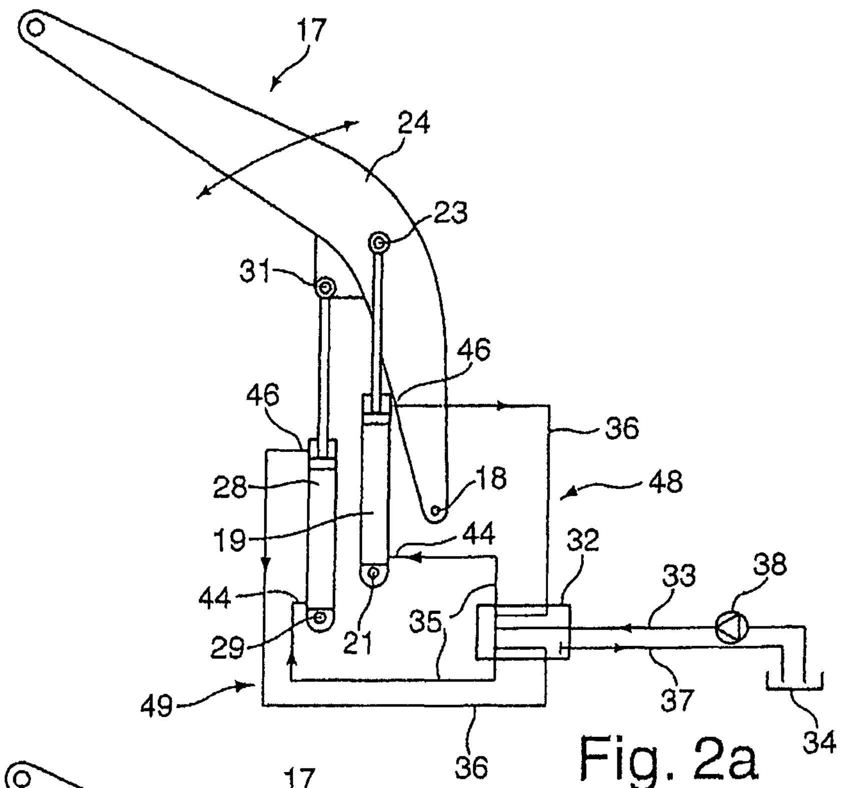

FIG. 2*a* is a schematic view of a hydraulic diagram of a hydraulic control device 32 of the working equipment 11 for actuating the lifting cylinder 19, 28. The pressure medium is fed from a tank 34, via an inlet 33 of the hydraulic control device 32 by means of a pump 38. Pressure medium to be carried off from the hydraulic control device 32 is fed back into the tank 34 via the discharge 37. The hydraulic control device 32 comprises hydraulic lines 35, 36 which, for example, can be interconnected via valves depending on the respective operating modes for different circuit arrangements, as will be described hereinafter in detail.

The main cylinder 19 and the additional cylinder 28 are designed as double-action lifting piston cylinders. These each comprise a connection 44 on the piston chamber side and a connection 46 on the piston rod side. The connection 44 on the piston chamber side is supplied starting from the control device 32 via a hydraulic line 35. The connection 46 on the piston rod side is connected via the hydraulic line 36 to the control device 32. Depending on the actuation of the main and additional cylinders 19, 28, the connection 44 on the piston chamber side may act as a pressurised connection, and the connection 46 on the piston rod side may act as an unpressurised connection. In such a case the lifting rod of the respective main and additional cylinder 19, 28 is extended. A swap may also be provided, that is to say the connections 46 on the piston rod side of the main and additional cylinder 19, 28 are pressurised connections and the connections 44 on the piston chamber side form the unpressurised connections. In such a case the lifting rods move in a cylinder housing of the respective main and additional cylinder 19, 28.

In order to move a working element, in particular a bearing arm 24, up and down or to pivot it, a rapid motion mode, a working motion mode and a heavy load motion load can be selectively actuated via the hydraulic control device 32.

Figure 2B:
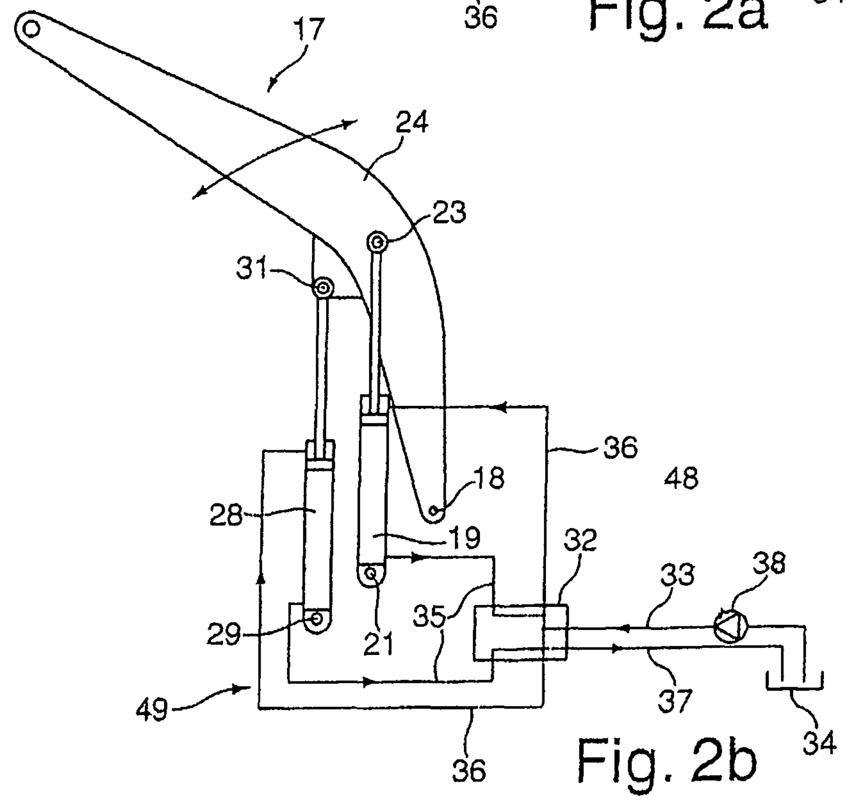

FIG. 2*a* shows a first circuit arrangement of the control device 32 for a first working pressure range, which controls the lifting of the bearing arm 24 in the rapid motion mode. FIG. 2*b* shows a lowering movement in the rapid motion mode.

In the case of this first circuit arrangement, pressure medium is fed via the inlet 33 and each of the connections 44 on the piston chamber side is operated as a pressurised connection. The pressure medium discharged on the piston rod side during the movement of extension of the main and additional cylinders 19, 28 is carried off via the connections 46 as unpressurised connections. The discharged pressure medium is fed back to the circuit arrangement 32 via the line 36, wherein the line 36 is bypassed in each case with the lines 35 so that a bypass circuit 48 is formed for the main cylinder 19 and, separately therefrom, a bypass circuit 49 is formed for the additional cylinder 28, whereby the discharged pressure medium is again fed directly on the piston chamber side. In addition, pressure medium can be fed to the respective bypass circuit 48, 49 via the line 33. As a result, the rapid motion mode can be actuated in the first working pressure range, and the at least one main cylinder 19 and at least one additional cylinder 28 can be moved with a high speed of travel. Owing to the bypass circuit 48, 49, a rapid filling on the pressurised side of the at least one main and additional cylinders 19, 28 is made possible. At the same time, there are low frictional losses in the lines 35, 36.

The lowering or downwards pivoting movement is carried out similarly, wherein the connections 46 on the piston rod side are now the pressurised connections, as is shown in FIG. 2*b*. During the movement of extension according to FIG. 2*a*, the outlet 39 to the tank 34 is closed. During the downwards movement according to FIG. 2*b*, the discharge 37 is connected to the tank 34 so that excess pressure medium is carried off when implemented in the pressure chamber on the piston rod side.

Figure 2C:
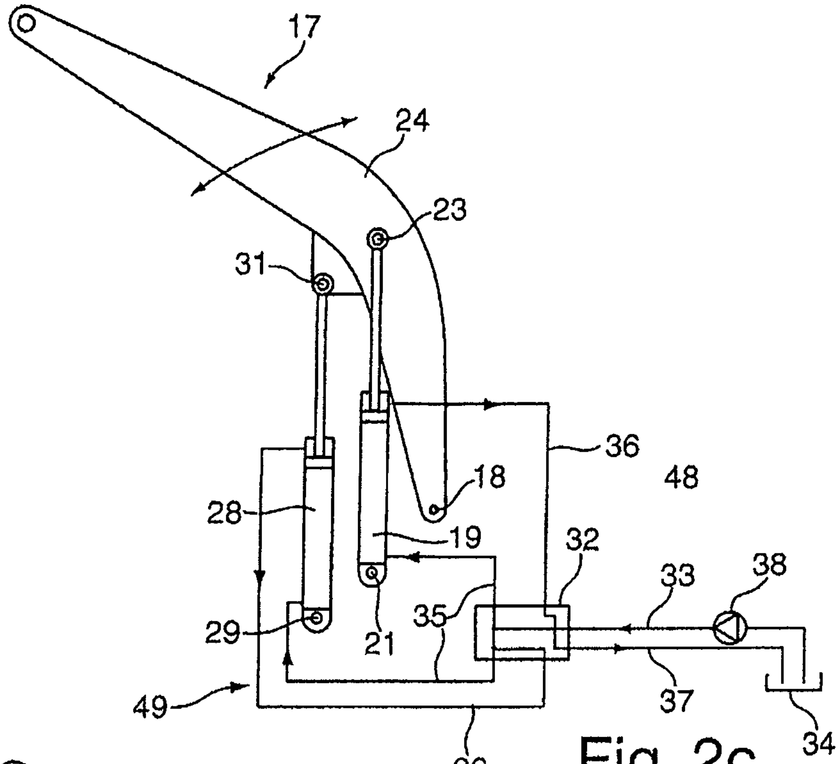

FIGS. 2*c* and *d* show a second circuit arrangement of the hydraulic control device 32 for actuating the at least one main cylinder and at least one additional cylinder 19, 28 in the working motion mode. Such a second circuit arrangement is adopted by the hydraulic control device as soon as a second working pressure range is detected by at least one control element. Such a control element may be a pressure sensor which is arranged in the hydraulic connection lines 35, 36 in a known manner. The second working pressure range is higher than the first working pressure range, and the second working range lies above the first working range.

The second circuit arrangement for the second working pressure range is provided in such a way that the bypass circuit 49 is actuated for the at least one additional cylinder 28, whereas the connections of the at least one main cylinder 19 are connected to the tank 34. In this second circuit arrangement the at least one main cylinder 19 is exposed to a working pressure to carry out the pivoting movement, whereas the at least one additional cylinder 28 is entrained in a force-free manner.

Figure 2D:
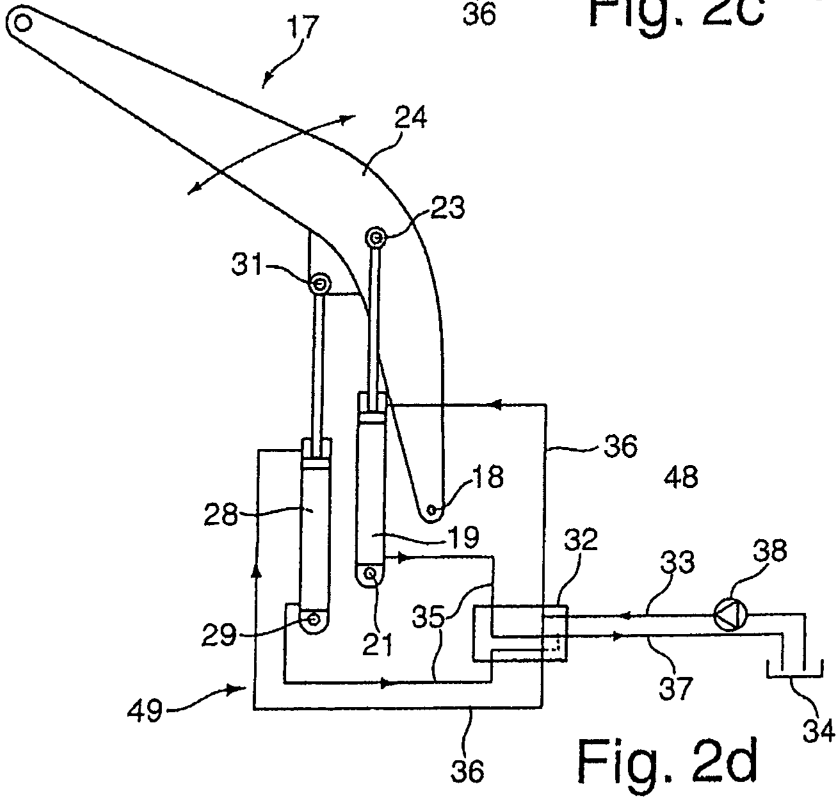

For example, FIG. 2*c* shows a movement of extension or an upwards movement of a bearing arm 24. FIG. 2*d* shows the downwards movement.

Figure 2E:
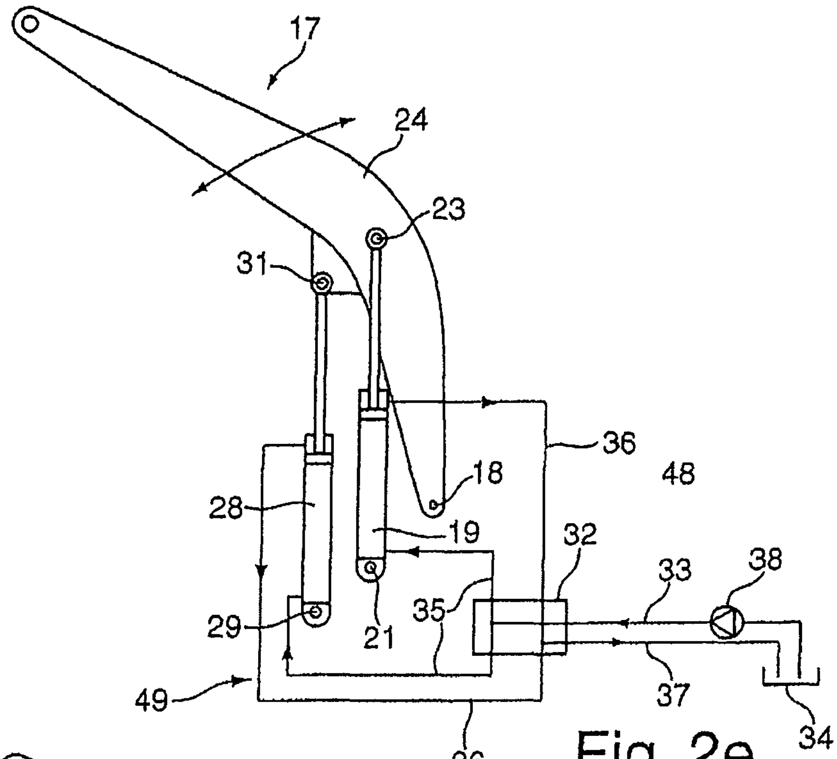

A third circuit arrangement is illustrated in FIGS. 2*e* and *f* and is adopted when the at least one control element detects a third working pressure range. The third working range comprises a working pressure which is higher than the prevailing working pressure of the first and second working pressure ranges. With this circuit arrangement both the connections 44, 46 of the at least one main cylinder 19 and the connections 44, 46 of the at least one additional cylinder 28 are connected to the tank 34 so that each pressurised connection 44 is supplied directly via the inlet 33 with pressure medium from the tank 34. With this third circuit arrangement the working element, in particular the bearing arm 24, is moved in the heavy load motion mode.

Figure 2F:
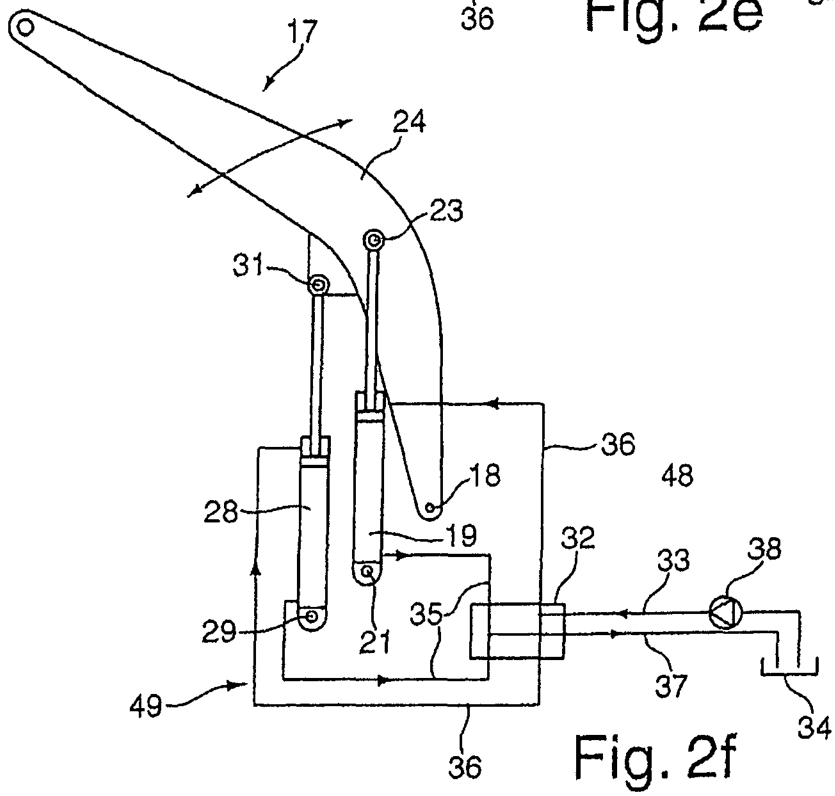

FIG. 2*e* shows the third circuit arrangement in the heavy load motion mode for an upwards movement, and FIG. 2*f* shows the third circuit arrangement in the heavy load motion mode for a downwards movement.

During a pivoting movement within the working range, as soon as the first presettable working pressure or the second presettable working pressure is exceeded or is undershot, the hydraulic control device 32 changes to the corresponding first, second or third circuit arrangement so that in each case an optimal actuation of the working element 24 is enabled within the pivoting range.

FIG. 3 shows a schematic side view of an alternative embodiment of the working equipment 11 according to FIGS. 1*a* and *b*. The at least one additional cylinder 28 is formed as a "stick cylinder" and is located on an opposite side of the boom 17, as is the case in FIGS. 1*a* and *b*.

FIGS. 4*a* and *b* show a further alternative embodiment of the attachment 11 in FIGS. 1*a* and *b*. By contrast, in this embodiment a multi-part boom 17 is provided. This boom 17 is, for example, formed in two parts and comprises a bearing arm stump 41 and a bearing arm portion 42, which are connected to one another in a replaceable manner via a changing device 43. In this embodiment the main cylinder 19 or the main cylinder pair and the at least one additional cylinder 28 engage with the bearing arm stump 41, and therefore this embodiment is completely identical to the embodiment according to FIGS. 1*a* and *b*, with the exception of the multi-part boom 17, and reference can therefore be made thereto. For example, in this embodiment the piston rods according to FIG. 4*a* are identically oriented and, for example, are oriented in the opposite direction according to FIG. 4*b*, that is to say in FIG. 4*b* the piston rods of the lifting cylinder 19 engage at the point of engagement 23, whereas the piston rod of the lifting cylinder 28 engages in the bearing axis 29. Alternatively, this arrangement can also be swapped.

FIG. 5 shows a schematic side view of an alternative embodiment compared to FIGS. 4*a* and *b*. Similarly to the alternative embodiment in FIG. 3, this alternative corresponds to FIGS. 1*a* and *b*. The at least one additional cylinder 28 is designed as a stick cylinder and engages with the bearing arm stump 41.

A further alternative embodiment compared to FIGS. 4*a* and *b* is shown in FIGS. 6*a* and *b*. This embodiment differs from FIGS. 4*a* and *b* in that the at least one additional cylinder 28 does not engage with the bearing arm stump 41, but with the bearing arm portion 42. In this embodiment the bearing arm portion 42 is designed as a crane having a lifting hook on a pulley block. For example, such an embodiment may be used to lay oil or water pipes. Since the insertion of the pipeline portions into trenches only accounts for some of the working time of such a working equipment 11, said outfit is retooled so that, for example, a bearing arm portion 42 according to FIGS. 4*a, b* and 5 is received and said working equipment 11 can then subsequently be used as an excavator or the like to dig the holes.

This embodiment according to FIGS. 6*a* and *b* is designed in such a way that, when the bearing arm portion 42 is changed, the bearing axis 29 of the additional cylinder 28 engaging with the revolving superstructure 11 is detached in such a way that the lifting cylinder 28 remains connected at its point of engagement 31 to the bearing arm portion 42. This lifting cylinder 28 may serve as a support when the bearing arm portion 42 is removed. In this embodiment a separate valve is preferably provided, in particular in the changing device 43, and can be switched on and off at the same time as the attachment and removal of the bearing arm portion 42.

FIG. 7 shows an alternative embodiment to FIGS. 6*a* and *b*. The additional cylinder 28 is designed as a stick cylinder instead of the lifting cylinder 28 between the lifting cylinders 19, and likewise in turn engages with the bearing arm portion 42.

The invention claimed is:

1. A method for actuating a hydraulically movable working element, which is provided on a main body of a working equipment, comprising at least one main cylinder and at least one additional cylinder, which are pivotably mounted on the main body and engage with the working element, by which the working element is actuated so as to be movable up and down in a working range, the main and additional cylinders each comprising a connection on the piston chamber side and a connection on the piston rod side and being supplied via pressure lines of a hydraulic control device and, in order to carry out a pivoting movement of the working element, being supplied with a pressure medium pressurised from a tank by means of pumps and in each case the connections on the piston chamber side or the connections on the piston rod side of the at least one main cylinder and the at least one additional cylinder being operated as pressurised connections, wherein the pivoting movement in the rapid motion mode is actuated in a first working pressure range of the hydraulic control device, the pivoting motion in a working motion mode is actuated in a second working pressure range, which is higher than the first working pressure range, the pivoting movement in the heavy load motion mode is actuated in a third working pressure range, which is higher than the first and second working pressure ranges, the pivoting movement of the working element in the operating modes of rapid motion, working motion or heavy load motion is actuated in accordance with the prevailing working pressure, and in the first working pressure range, in which the pivoting movement is actuated in the rapid motion mode, the pressure medium is fed from a tank of the working equipment to each of the pressurised connections of the at least one main and additional cylinders, and in that the unpressurised connections of the respective main and additional cylinders are connected to the associated pressurised connection by a respective bypass circuit so that in each case the pressure medium discharged from the main and additional cylinders is carried off via the unpressurised connections and is fed to the respective pressurised connections of the same main and additional cylinders.

2. The method according to claim 1, wherein in the second working pressure range, in which the pivoting movement is actuated in the working motion mode, the pressure medium is fed from the tank to the pressurised connection of the at least one main cylinder, the unpressurised connection of the main cylinder is connected to the tank to carry off the discharged pressure medium, and a bypass circuit is formed between the unpressurised and pressurised connections of the additional cylinder.

3. The method according to claim 1, wherein in the third working pressure range, in which the pivoting movement is actuated in the heavy motion mode, the pressure medium is fed from the tank to each of the pressurised connections of the at least one main cylinder and the at least one additional cylinder, and the unpressurised connections of the at least one main cylinder and the at least one additional cylinder for returning the pressure medium are connected to the tank.

4. The method according to claim 1, wherein the working pressure is monitored during the pivoting movement of the working element in the working range, and a first working pressure value is preset between the first and second working pressure ranges, and a second working pressure value is preset between the second and third working ranges, and in that if the respective working pressure value is exceeded or is not met, the corresponding operating mode is actuated.

5. The method according to claim 1, wherein the at least one additional cylinder is actuated during the pivoting movement of the working element as a damping cylinder which counteracts the main cylinder or main cylinder pair which carries out the lowering movement.

6. A working equipment comprising a hydraulically movable working element which is pivotably mounted on a main body, comprising at least one main cylinder and at least one additional cylinder which are pivotably mounted on the main body and engage with the working element, by which the working element is actuated so as to be movable up and down in a working range, the main and additional cylinders each comprising a connection on the piston chamber side and a connection on the piston rod side and being supplied with a pressure medium from a tank via pressure lines of a hydraulic control device, which pressure medium is pressurised by a pump, wherein the hydraulic control device comprises a first circuit arrangement in which the working element is actuatable in the rapid motion mode, a second circuit arrangement in which the working element is actuatable in the working motion mode, a third circuit arrangement in which the working element is actuatable in a heavy load motion mode, and at least one control element which controls the respective circuit arrangement, and in the first circuit arrangement the unpressurised connections of the at least one main and additional cylinders are connected to the pressurised connections of the same main and additional cylinders, and in each case form a bypass circuit for returning the discharged medium of the main and primary cylinders via the pressurised connection in the same main and additional cylinders.

7. The working equipment according to claim 6, wherein in the second circuit arrangement the pressurised connection and unpressurised connection of the at least one main cylinder are connected to the tank, and the unpressurised connection and the pressurised connection of the at least one additional cylinder are arranged in a bypass circuit.

8. The working equipment according to claim 6, wherein in the third circuit arrangement the pressurised connection and the unpressurised connection of the at least one main cylinder and the unpressurised connection and pressurised connection of the at least one additional cylinder are connected to the tank.

9. The working equipment according to claim 6, wherein additional pressure medium is fed by a supply line to the respective bypass circuits of the at least one main cylinder, or additional cylinder, or both.

10. The working equipment according to claim 6, wherein the at least one main cylinder comprises a point of engagement with the working element which is different from the point of engagement of the at least one additional cylinder.

11. The working equipment according to claim 6, wherein the longitudinal axis of the at least one additional cylinder is arranged between the working element formed as a bearing arm and the main body formed as a revolving superstructure at a different angle from a longitudinal axis of the at least one main cylinder.

12. The working equipment according to claim 6, wherein the longitudinal axis of the at least one additional cylinder is oriented parallel to the longitudinal axis of the at least one main cylinder.

13. The working equipment according to claim 6, wherein the working element is formed as a bearing arm and the bearing arm of the boom is formed in a number of parts comprising a bearing arm stump and at least one bearing arm portion, and comprises a changing device, and the at least one additional cylinder engages with a bearing arm stump of the bearing arm.

14. The working equipment according to claim 13, wherein the bearing arm of the boom is formed in a number of parts and comprises a changing device, and the at least one additional cylinder engages with the replaceable bearing arm portion of the bearing arm.

15. The working equipment according to claim 13, wherein the at least one additional cylinder arranged on the bearing arm portion remains connected to the bearing arm portion when said bearing arm portion is changed.

16. The working equipment according to claim 13, wherein an additional valve for actuating the at least one additional cylinder is provided on the replaceable bearing arm portion, in particular in the region of the changing device.

17. The working equipment according to claim 6, wherein the at least one additional cylinder is arranged adjacent to the at least one main cylinder or between two main cylinders.

18. The working equipment according to claim 6, wherein the at least one additional cylinder is arranged as a stick cylinder between the main body designed as a revolving superstructure and the bearing arm working element.

19. The working equipment according to claim 13, wherein, in the case of a multi-part boom comprising at least two bearing arms arranged so as to be pivotable in relation to one another, at least one additional cylinder is arranged between two bearing arms and comprises, in contrast to the at least one main cylinder, a lever arm between the two bearing arms.

20. The working equipment according to claim 6, wherein the at least one additional cylinder is arranged as a stick cylinder between the main body designed as a revolving superstructure and the working element designed as a bearing arm.

* * * * *